(12) United States Patent
Rejai

(10) Patent No.: US 6,886,443 B2
(45) Date of Patent: May 3, 2005

(54) APPARATUS AND METHOD FOR MAKING A TAMPON APPLICATOR

(75) Inventor: Jamshid Rejai, Dover, DE (US)

(73) Assignee: Playtex Products, Inc., Westport, CT (US)

( * ) Notice: Subject to any disclaimer, the term of this patent is extended or adjusted under 35 U.S.C. 154(b) by 54 days.

(21) Appl. No.: 10/184,040

(22) Filed: Jun. 26, 2002

(65) Prior Publication Data

US 2004/0000222 A1 Jan. 1, 2004

(51) Int. Cl.[7] .............................................. B26D 11/00
(52) U.S. Cl. ............................ 83/862; 83/864; 83/879; 83/883
(58) Field of Search ......................... 83/879, 880, 883, 83/98, 100, 684, 687, 55, 862, 188, 54, 192–194, 864; 28/118–120

(56) References Cited

U.S. PATENT DOCUMENTS

| | | | | |
|---|---|---|---|---|
| 2,600,971 A | | 6/1952 | Collins et al. | |
| 3,374,697 A | * | 3/1968 | Robinson | 83/35 |
| 3,485,124 A | * | 12/1969 | Merchant | 83/182 |
| 3,763,729 A | * | 10/1973 | Ashby | 83/37 |
| 4,257,293 A | * | 3/1981 | Stahl | 83/193 |
| 4,453,925 A | | 6/1984 | Decker | 604/14 |
| 4,778,374 A | | 10/1988 | Takahashi et al. | 425/343 |
| 5,211,093 A | * | 5/1993 | Horniak | 83/426 |
| 5,290,501 A | | 3/1994 | Klesius | 264/322 |
| 5,389,067 A | | 2/1995 | Rejai | 604/14 |
| 5,564,319 A | * | 10/1996 | Kowal | 82/46 |
| 5,571,540 A | | 11/1996 | Weyenberg et al. | 425/343 |
| 5,699,708 A | * | 12/1997 | Deni et al. | 83/180 |
| 6,079,078 A | * | 6/2000 | Byington | 15/339 |
| 6,095,999 A | | 8/2000 | Jackson et al. | 604/14 |
| 6,511,451 B1 | * | 1/2003 | Schoelling et al. | 604/14 |

* cited by examiner

*Primary Examiner*—Kenneth E. Peterson
*Assistant Examiner*—Omar Flores Sánchez
(74) *Attorney, Agent, or Firm*—Ohlandt, Greeley, Ruggiero & Perle, LLP

(57) ABSTRACT

There is provided a tampon applicator apparatus and method for creating and scoring petals or petal tips of the tampon applicator. The apparatus has a holding element for the tampon applicator, a score device for forming a score line at the base of the petals, and two or more punch devices for creating a petal. There is also provided a vacuum for removing the portions of the tampon applicator that are punched out.

37 Claims, 5 Drawing Sheets

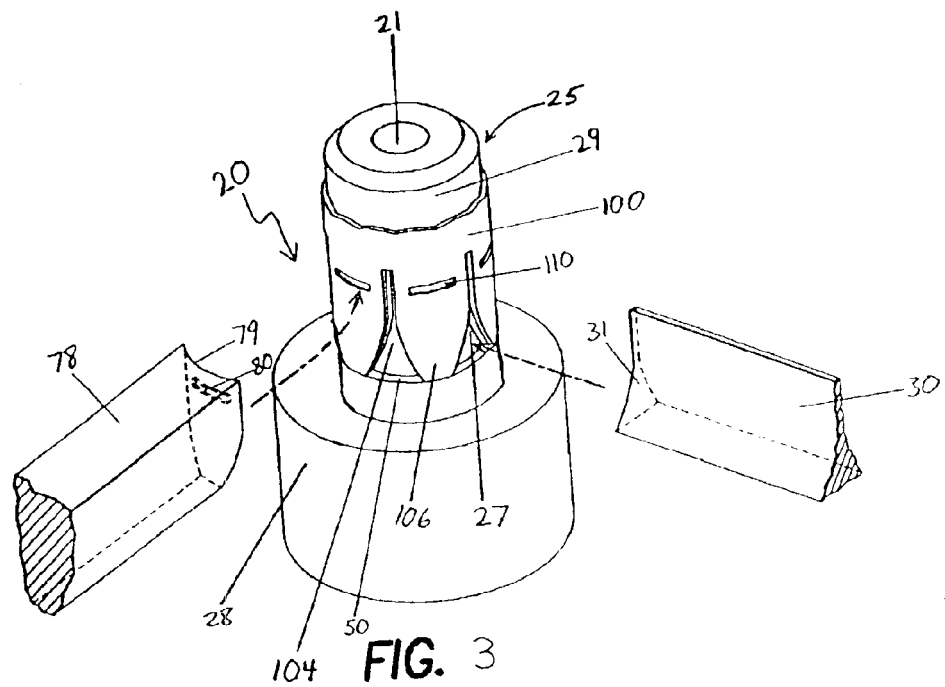
FIG. 3
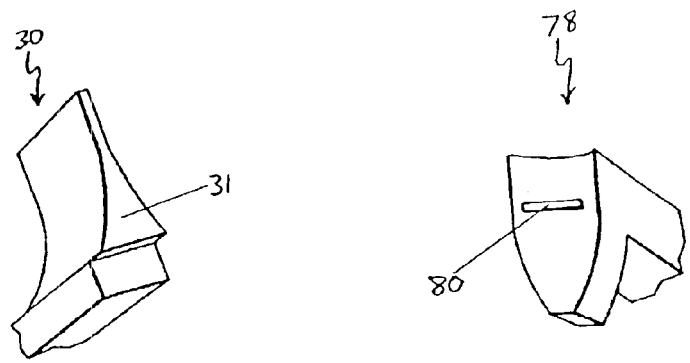
FIG. 4
FIG. 5

APPARATUS AND METHOD FOR MAKING A TAMPON APPLICATOR

BACKGROUND OF THE INVENTION

1. Field of the Invention

The present invention relates to an apparatus for making a tampon applicator and a method for making same. More particularly, the present invention relates to an apparatus for making a cardboard or paper-like tampon applicator having petal-like segments or petal tips. By this apparatus, the petal-like segments are created with one or more perforation lines at the base of the petal-like segments. The present invention also includes a method of making the tampon applicator using this apparatus.

2. Description of the Prior Art

A variety of commercial tampon applicators available on the market are formed from paper, cardboard or other pulp-based materials, such as paperboard or paper laminate (collectively referred to as "cardboard"). Many of these commercial products have petal-like segments or petal-tips at the tampon ejection end of the applicator. In some commercial products, the petals are formed into a dome shape over the leading edge of the pledget. The resulting rounded shape is perceived as easier to insert than the blunt-end tampon applicators known in the art, and the petals also protect the pledget.

The use of such petal-tip applicators results in an increase in the pressure necessary to open the petals during expulsion of the pledget from the tampon applicator. The user must push the applicator plunger with sufficient force to move the pledget forward to open the petals and then pass over the opened petals. If too much pressure or force is required, the tampon applicator will be less acceptable to the consumer.

A variety of methods have been employed to address this issue. Most methods involve the partial perforation, score line, or weakening of the cardboard, either at the base of the petal, or at some portion of the petal nearer to the tip. However, the perforation or weakening process requires costly and exacting multiple manufacturing steps. There exists a need for a single apparatus or device to economically and efficiently punch or create petals in the barrel of the cardboard tampon applicator, to add one or more perforation lines at the base of the petals, and to preferably also automatically remove the discarded cardboard pieces.

SUMMARY OF THE INVENTION

It is an object of the present invention to provide an apparatus for making a cardboard tampon applicator having petal-like segments or petal tips.

It is another object of the present invention to provide such a device that creates the petals and also forms or adds one or more perforation lines at the base of the petals.

It is still another object of the present invention to provide such a device in which the perforation lines at the base of the petals weaken the petals to allow for a decrease in the force applied to open the petals and expel the pledget from the tampon applicator.

It is a further object of the present invention to provide for such an apparatus that creates the petals, forms or adds the one or more perforation lines at the base of the petals, and removes discarded cardboard.

It is a still further object of the present invention to provide a method of making a cardboard or paper-like tampon applicator using the apparatus of the present invention.

These and other objects and advantages of the present invention are achieved by an apparatus of the present invention that makes a cardboard or paper-like tampon applicator. The apparatus has a holding element, preferably a mandrel die, with a center portion for positioning and securing the tampon applicator with said holding element having more than two radially projecting spokes, a plurality of punch devices positioned on some spokes of the mandrel die, and one or more perforating or score devices positioned on one or more of the other spokes of the mandrel die. Each punch device and each score device has a portion that is adapted to move on its respective spoke toward the positioned tampon applicator to strike the tampon applicator. The apparatus also pneumatically activates the punch elements to form petals on the leading end of the tampon applicator and the perforating or scoring elements to form score lines almost simultaneously. The apparatus also has a vacuum device connected to the lower portion of the hollow mandrel die to suction away unused cardboard from the mandrel die.

BRIEF DESCRIPTION OF THE DRAWINGS

These and other embodiments of the present invention will be appreciated by referring to the drawings

FIG. 3 is a schematic view of a punch tool and a scoring tool in open position with a cutaway view of a tampon applicator blank on the mandrel die of the tampon applicator apparatus of FIG. 1;

FIG. 4 is a perspective view of a punch tool for the tampon applicator apparatus of FIG. 1;

FIG. 5 is a perspective view of a scoring tool for the tampon applicator apparatus of FIG. 1;

DESCRIPTION OF THE INVENTION

Figure 1:
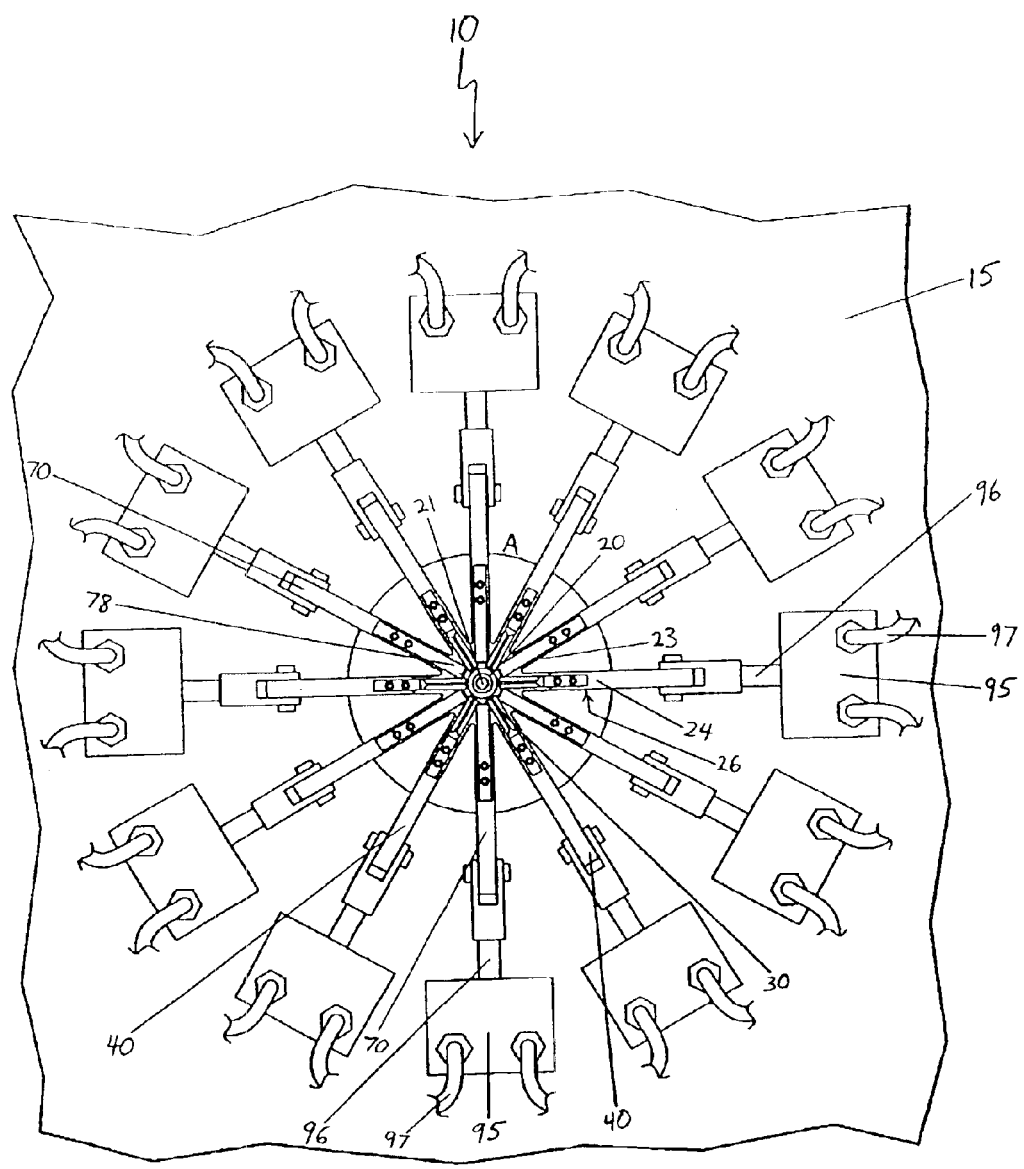
FIG. 1 is a top view of the tampon applicator apparatus of the present invention.
Figure 2:
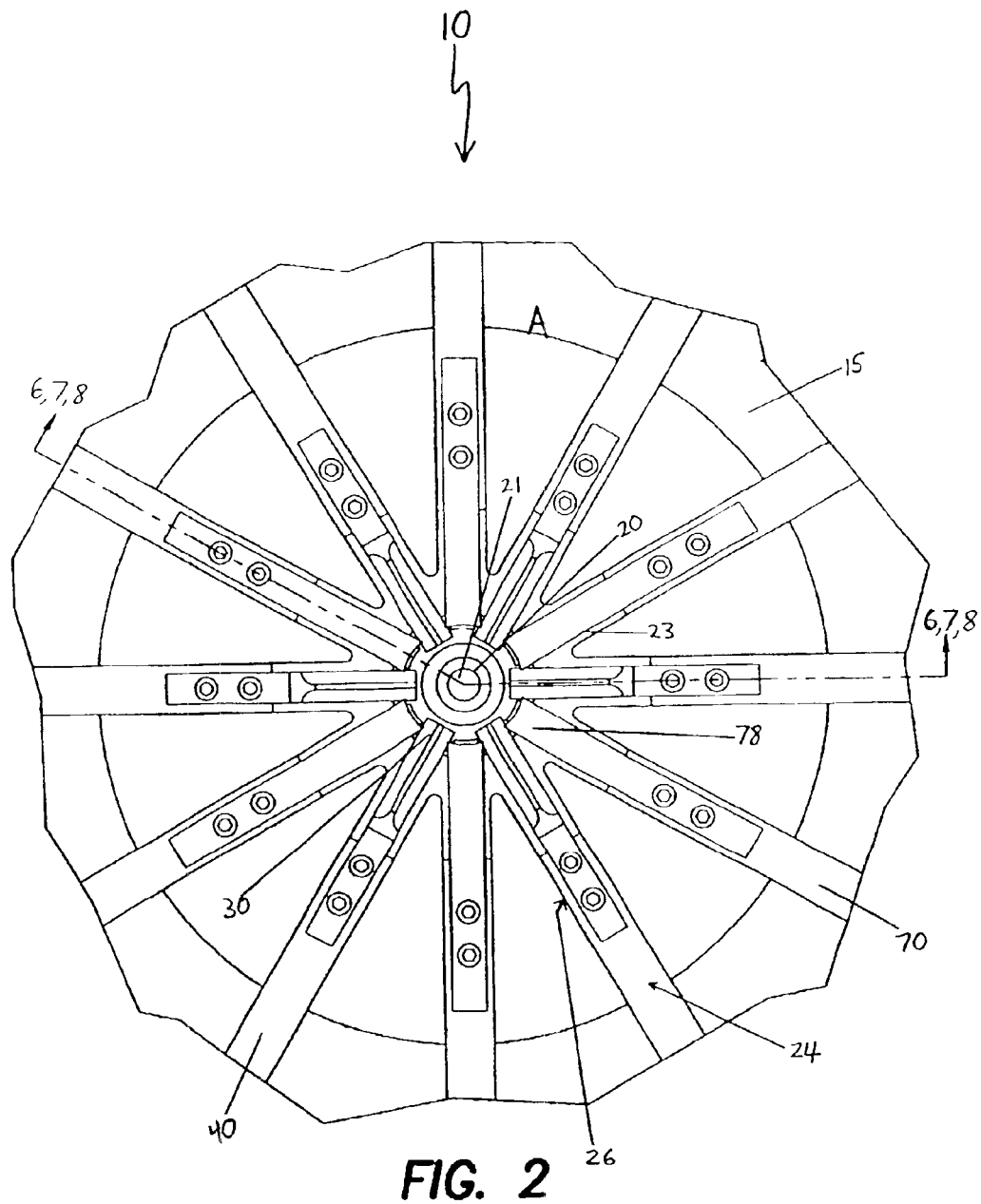
FIG. 2 is an exploded view of area A of the tampon applicator apparatus of FIG. 1.

Referring to the drawings and, in particular, FIGS. 1 and 2, there is shown a tampon applicator apparatus generally represented by reference numeral 10. Apparatus 10 has a generally circular configuration with mandrel die 20 positioned at its center. Preferably, mandrel die 20 has a body 25 that is generally cylindrical in shape. The body 25 has a cylindrical hollow center portion 21 that extends along the central longitudinal axis of the mandrel die, and several radially extending spokes 23. Mandrel die 20 with two or more webs or spokes 23, two or more punch slides 40 aligned with and positioned along several spokes of the mandrel die, and one or more perforation or score slides 70 aligned with and positioned on other spokes of the mandrel die. The apparatus 10 has double acting air cylinders 95 that actuate connection elements 96 that are operatively connected to punch slides 40 and score slides 70. Air cylinders 95 have air lines 97, each actuating punch slides 40 and perforation or score slides 70 toward inward or outward directions. Although punch slides 40 and score slides 70 are preferably actuated by air cylinders 95 and air lines 97, actuation can also be achieved by using cams, electrical means such as an electric motor, or any other suitable actuation means. Apparatus 10 may have a base frame 15 on which mandrel die 20, connection elements 96 and air cylinders 95 are mounted for positional movement. Base frame 15 is preferably a metal board.

Referring to FIG. 3, body 25 has a lower portion 28, an upper portion 29 and a step 50 that connects the lower to the upper portion. Referring to FIGS. 1 and 2, each spoke 23 has an upper surface 24 with a slide channel 26 therein. Preferably, the number of spokes 23 is six to sixteen. More preferably, the number of spokes 23 is twelve.

In the discussion that follows, the term "proximal," will refer to the portion of the structure that is closer to mandrel die 20. The term "distal" will refer to the portion that is further from mandrel die 20.

As shown in FIGS. 1 through 3, some spokes 23 have connected thereto, preferably removably, punch slides 40, while all or some of the remaining spokes have connected thereto, preferably removably, perforation or score slides 70. The punch slides 40 and score slides 70 are arranged also in a radial configuration on spokes 23 of mandrel die 20. The arrangement and number of punch slides 40 correspond to the position and number, respectively, of petals desired in the ejection end of a tampon applicator or applicator blank 100, shown in FIG. 3. The number of score slides 70 correspond to the number of separate score lines on the base of the petals in applicator 100. It should be understood that there can be as little as one score line per petal in the tampon applicator and, thus, just one score slide 70 would be needed for each petal. In a more preferred embodiment, there is a score slide 70 placed on each spoke 23 that does not have a punch slide 40 since the greater the number of perforations or score lines, the less force needed to move the formed petals during the tampon ejection process. As shown in the preferred embodiment of FIGS. 1 and 2, punch slides 40 and score slides 70 are on alternating spokes 23 of mandrel die 20. Thus, each score slide 70 has a corresponding punch slide 40 positioned on the other spoke 23 of mandrel die 20 on the same longitudinal axis. It should be understood that two or more score edges 80 could be on a single score tool 78 to form two circumferentially parallel score lines within the base of the petal in tampon applicator 100.

As shown in FIGS. 2 and 3, each punch slide 40 has a punch tool 30. Preferably, punch slide 40 is elongated. Each punch slide 40 is secured to a separate spoke 23. Each punch tool 30 is connected, preferably removably, to its respective punch slide 40, by any conventional fastener.

Each punch slide 40 can be located in respective slide channel 26 in spoke 23. Each slide channel 26 extends from the distal end of a punch slide 40, to the mandrel die 20. The channel 26 provides for sliding movement of punch slide 40. The distal end of each punch slide 40 is connected to air cylinder connection elements 96 to provide conventional power to move the punch arm in sliding movement in slide channel 26.

Figure 7:
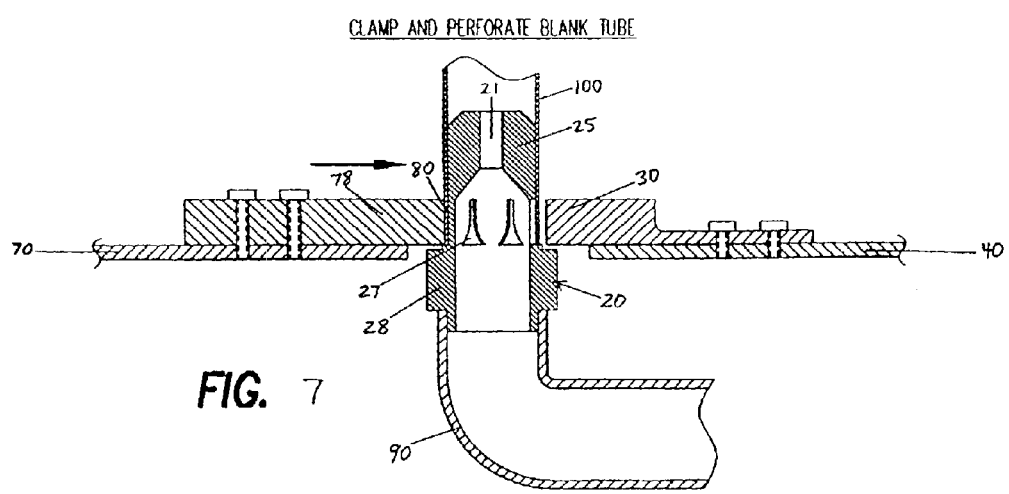
FIG. 7 is a cross-sectional view of the tampon applicator apparatus of FIG. 2 taken along line 7—7, with a scoring tool actuated for holding the tampon applicator blank and scoring the blank.

Referring to FIGS. 3 and 4, each punch tool 30 is generally the contour of a petal and has an exterior face 31 that has the contour of a petal in the tampon applicator blank 100. As shown in FIG. 7, punch tool 30 is slightly offset from punch slide 40 so that face 31 projects beyond the body of the punch tool, thereby permitting the face to punch its shape into tampon applicator or applicator blank 100 to separate the cardboard. Tampon applicator 100 then has a separation or space 104 that matches face 31 and thus forms an edge of two adjacent petals 106.

Referring to FIGS. 3 and 5, each score slide 70 has a score tool 78. Preferably, score slide 70 is elongated. The distal end of each score tool 78 is connected, preferably removably, by any conventional fastener, to the proximal end of each score slide 70. Each score slide 70 can slidingly move in its channel 26 in spoke 23 in the direction defined by its longitudinal axis. Similar to each punch slide 40, the distal end of each score slide 40 is connected by air cylinder connection elements 96, double acting air cylinder 95 and air lines 97 to an air supply to permit movement of the score slide 70 in channel 26 of its respective spoke 23.

Each score tool 78 has a contoured proximal surface 79 that is configured to engage applicator blank 100. Each proximal surface 79 has a protruding generally contour-shaped perforating or score edge 80 that is configured to radially engage the outside surface of the tampon applicator blank 100.

Figure 6:
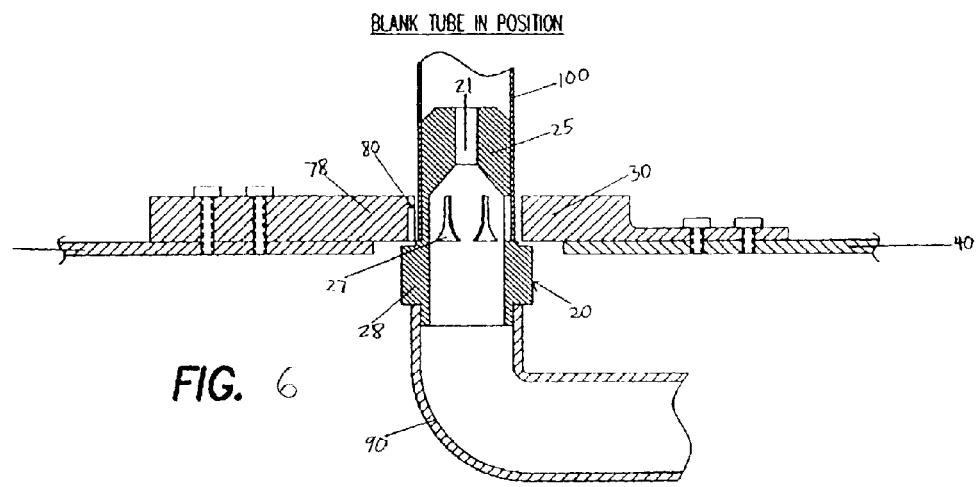
FIG. 6 is a cross-sectional view of the tampon applicator apparatus of FIG. 2 taken along line 6—6, with the tampon applicator blank in position on the mandrel die.
Figure 8:
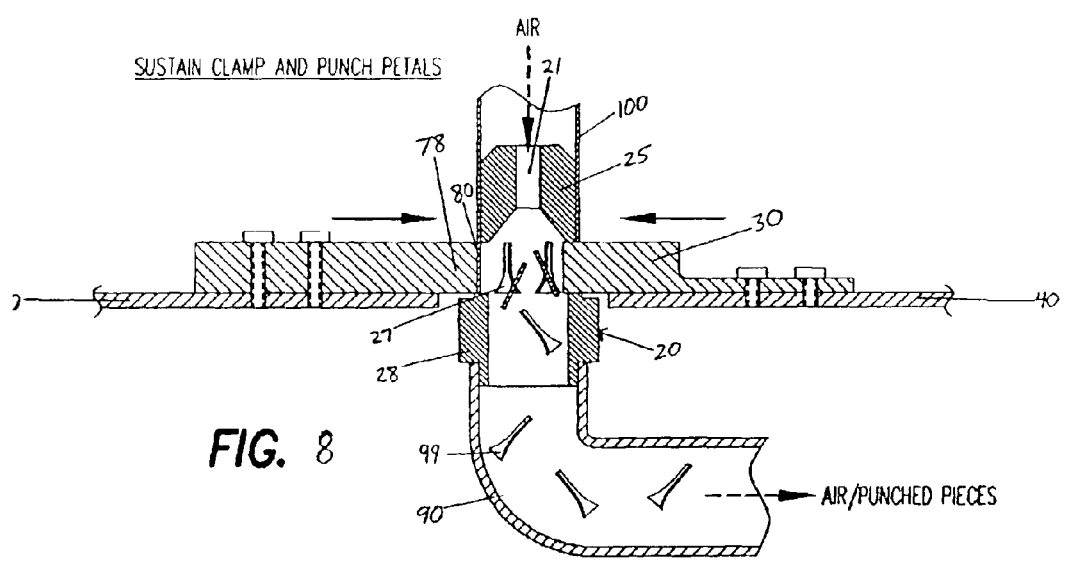
FIG. 8 is a cross-sectional view of the tampon applicator apparatus of FIG. 2 taken along line 8—8, with a punch tool actuated and the blank held by the scoring element, and unused punched out pieces being vacuumed out of the apparatus.

Referring to FIGS. 6 to 8, tampon applicator apparatus 10 includes a vacuum device, such as a tube 90. In a preferred embodiment shown in FIG. 3, the proximal end of vacuum tube 90 is connected to the bottom end of mandrel die 20, through an opening in base frame 15. The proximal end of vacuum tube 90 fits over a bottom opening in mandrel die 20. Preferably, the distal end of vacuum tube 90 is connected to a vacuum generator device and a receptacle.

In using tampon applicator apparatus 10, tampon applicator blank 100 is positioned about cylindrical hollow central portion 21 of mandrel die 20 as shown in FIG. 3. The diameter of tampon applicator or applicator blank 100 is similar to the diameter of upper portion 29 of body 25 of mandrel die 20, while still allowing the tampon applicator blank to fit about the upper surface of the upper portion. As shown in FIG. 3, tampon applicator blank 100 is placed about upper portion 29 of body 25 of mandrel die 20 with the blank's proximal lip resting on step 50 of mandrel die 20. Step 50 has a width close to the paper thickness of tampon applicator blank 100 that allows for an end of applicator blank 100 to rest on step 50.

After tampon applicator blank 100 is positioned onto mandrel die 20, tampon applicator apparatus 10 is activated. Activation of tampon applicator apparatus 10 results initially in clamping and perforation of tampon applicator blank 100. As shown in FIG. 7, score slides 70 are actuated and all slide about simultaneously towards the upper portion 29 of body 25 of mandrel die 20. All score tools 78 simultaneously, or approximately simultaneously, strike tampon applicator blank 100 radially. Each score tool 78 produces a separate score line 110 in the cardboard at the location of impact. Preferably, six perforated score lines 110 are created. At the same time, score slides 70 clamp tampon applicator blank 100, as shown in FIG. 7.

As shown in FIG. 8, after a slight delay in timing after perforating or scoring and clamping action, punch slides 40 are actuated. While the clamp is sustained, all punch slides 40 slide simultaneously, or approximately simultaneously, towards the upper portion 29 of body 25 of mandrel die 20. Each punch tool 30 simultaneously, or approximately simultaneously, strikes tampon applicator blank 100 radially so that each exterior face 31 of each punch tool 30 cuts through the cardboard of the tampon applicator blank to form space 104 and enters an aligned triangle shaped groove 27 in the upper portion 29 of body 25 of mandrel die 20. Exterior face 31 of punch tool 30 can mate with triangle shaped groove 27 on upper portion 29, to make a clean punch or space 104 on the surface of applicator blank 100. This action punches or cuts triangular space 104 in tampon applicator blank 100 that is in the shape of triangle shaped groove 27 behind it. Preferably, six triangular shaped spaces with contoured sides 104 are simultaneously, or almost simultaneously, created. As shown in FIG. 8, the punched cardboard pieces 99 are pushed into the hollow tube of mandrel die 20, and are suctioned away from tampon applicator apparatus 10 through vacuum tube 90, as air is suctioned into mandrel die 20 through its top opening. Punch tools 30 are withdrawn first, and then score tools 78 are withdrawn away from mandrel die 20.

As shown in FIG. 3, the base of each of the six triangular shaped holes in tampon applicator blank 100 is proximally located. These spaces 104 create six generally triangular petals 106 in the cardboard at the proximal end of tampon applicator blank 100. Each score line 110 was formed at the distal end base of each petal 106 as shown in FIG. 3. The tampon applicator blank 100 can subsequently undergo further processing to form petals 106 into a domed, tapered, or other shape, and to assemble the remaining components of the tampon.

The present invention having been thus been described with particular reference to the preferred forms thereof, it will be obvious that various changes and modifications may be made therein without departing from the spirit and scope of the present invention as defined in the appended claims.

What is claimed is:

1. An apparatus for creating and scoring petals of a tampon applicator virtually simultaneously, the apparatus comprising:
   a holding element having a center portion for positioning and securing the tampon applicator, said holding element having more than three radially projecting spokes;
   at least two punch devices, each of said at least two punch devices having a punch arm positioned for sliding on a separate one of the more than three spokes toward the tampon applicator to strike the tampon applicator and create a petal; and
   a score device having a score arm positioned for sliding on a remaining one of said more than three spokes toward the tampon applicator to score the tampon applicator.

2. The apparatus of claim 1, wherein the holding element is a mandrel die.

3. The apparatus of claim 1, wherein the at least two punch devices is at least four punch devices.

4. The apparatus of claim 1, wherein the at least two punch devices is at least five punch devices.

5. The apparatus of claim 1, wherein the at least two punch devices is at least six punch devices.

6. The apparatus of claim 1, wherein the score device is a plurality of score devices, wherein the at least two punch devices is a plurality of punch devices, and wherein the plurality of score devices equals the plurality of punch devices.

7. The apparatus of claim 1, wherein the score device is four score devices.

8. The apparatus of claim 1, wherein the score device is five score devices.

9. The apparatus of claim 1, wherein the score device is six score devices.

10. The apparatus of claim 1, wherein the tampon applicator is made from a pulp based material.

11. The apparatus of claim 1, wherein the tampon applicator is made from a combination of pulp and non-pulp based materials.

12. The apparatus of claim 1, further comprising an actuator for conveying power from a power source to slide said punch arms of the at least two punch devices towards the tampon applicator.

13. The apparatus of claim 12, wherein said actuator is selected from the group consisting of air cylinder, cam, electric motor, and any combination thereof.

14. The apparatus of claim 1, further comprising an actuator for conveying power from a power source to slide said score arm towards the tampon applicator.

15. The apparatus of claim 14, wherein said actuator is selected from the group consisting of air cylinder, cam, electric motor, and any combination thereof.

16. The apparatus of claim 1, wherein the tampon applicator is made from non-pulp based materials.

17. The apparatus of claim 16, wherein said non-pulp material is selected from the group consisting of biopolyrner, plastic, thermoplastic polymer, thermosetting polymer, and any combinations thereof.

18. The apparatus of claim 1, wherein the tampon applicator has a first end, and wherein said punch arms of the at least two punch devices strike the first end of the tampon applicator to remove applicator material from the tampon applicator and form a plurality of petals.

19. The apparatus of claim 18, wherein the score device has a portion that strikes the tampon applicator to compress or partially cut through the applicator material and form a score line in the base of the plurality of petals.

20. The apparatus of claim 19, further comprising a vacuum for removing applicator material away from the holding element.

21. The apparatus of claim 1, wherein the score device is a plurality of score devices.

22. The apparatus of claim 21, wherein each of the more than three spokes has a channel.

23. The apparatus of claim 22, wherein each of the at least two punch devices has the punch arm and a punch tool, and wherein the punch arm is adapted to slide in the channel.

24. The apparatus of claim 22, wherein the score device has the score arm and a score tool, and wherein the score arm is adapted to slide in the channel.

25. The apparatus of claim 1, wherein the holding element is a mandrel die having the more than three spokes.

26. The apparatus of claim 25, wherein the score device is a plurality of score devices, wherein the at least two punch devices is a plurality of punch devices, and wherein the plurality of score devices equals the plurality of punch devices.

27. The apparatus of claim 25, wherein each of the plurality of score devices and each of the plurality of punch devices are positioned on a separate one of the plurality of spokes.

28. The apparatus of claim 27, wherein each of the plurality of score devices is located between each adjacent pair of the plurality of punch devices.

29. The apparatus of claim 1, wherein each of the at least two punch devices has a punch tool.

30. The apparatus of claim 29, wherein the punch tool is linearly connected to the punch arm.

31. The apparatus of claim 29, wherein each of the punch tools of the at least two punch devices can radially engage the holding element.

32. The apparatus of claim 29, wherein each of the punch tools of the at least two punch devices has a generally contoured cutting edge that is configured to radially contact the holding element.

33. The apparatus of claim 1, wherein the score device has a score tool.

34. The apparatus of claim 33, wherein the score tool is linearly connected to the score arm.

35. The apparatus of claim 33, wherein the score tool can radially engage the holding element.

36. The apparatus of claim 33, wherein the score tool has a protruding generally linear shaped score edge that is configured to radially engage an applicator blank against the holding element.

37. An apparatus for creating and scoring petals of a tampon applicator blank substantially simultaneously, the apparatus comprising:

a first longitudinal member with a center, the tampon applicator blank being held on said first longitudinal member;

a plurality of first radially projecting members, each of said plurality of first radially projecting members being radially disposed around said center; and a plurality of second radially projecting members, each of said plurality of second radially projecting members being radially disposed around said center, each of said plurality of second radially projecting members having a first arm with a first tool, said first arm being positioned for selectively sliding on said plurality of second radially projecting members, said first arm eliding in a direction toward the tampon applicator blank, said first tool striking the tampon applicator blank for creating the petal on the tampon applicator blank, wherein each of said plurality of first radially projecting members has a second arm with a second tool, said second arm for selectively sliding in said direction toward the tampon applicator blank, said second tool forming a score on or in the tampon applicator blank, said score being a substantially orthogonal shaped notch.

* * * * *